(12) United States Patent
Muller et al.

(10) Patent No.: US 11,701,088 B2
(45) Date of Patent: Jul. 18, 2023

(54) SYSTEMS, METHODS, AND DEVICES FOR INSTRUMENT GUIDANCE

(71) Applicant: Ethos Medical, Inc., Atlanta, GA (US)

(72) Inventors: Lucas Muller, Atlanta, GA (US); Cassidy Wang, Atlanta, GA (US); Dev Mandavia, Atlanta, GA (US)

(73) Assignee: Ethos Medical, Inc., Atlanta, GA (US)

( * ) Notice: Subject to any disclaimer, the term of this patent is extended or adjusted under 35 U.S.C. 154(b) by 0 days.

(21) Appl. No.: 16/816,363

(22) Filed: Mar. 12, 2020

(65) Prior Publication Data
US 2020/0281563 A1 Sep. 10, 2020

Related U.S. Application Data

(63) Continuation of application No. 16/810,569, filed on Mar. 5, 2020, now abandoned.
(Continued)

(51) Int. Cl.
*A61B 8/00* (2006.01)
*A61B 34/20* (2016.01)
*A61B 8/08* (2006.01)

(52) U.S. Cl.
CPC .......... *A61B 8/4254* (2013.01); *A61B 8/0841* (2013.01); *A61B 8/4209* (2013.01);
(Continued)

(58) Field of Classification Search
USPC ....................................................... 600/439
See application file for complete search history.

(56) References Cited

U.S. PATENT DOCUMENTS

| | | |
|---|---|---|
| 4,431,006 A | 2/1984 | Trimmer et al. |
| 4,469,106 A | 9/1984 | Jarui |

(Continued)

FOREIGN PATENT DOCUMENTS

| | | |
|---|---|---|
| EP | 0550069 A1 | 7/1993 |
| JP | 2016106009 A | 6/2016 |
| JP | 2018012001 A | 1/2018 |

OTHER PUBLICATIONS

"What is RFID?". BarCode Graphics, Inc: 2020. (Year: 2020).*
(Continued)

*Primary Examiner* — Jason M Ip
*Assistant Examiner* — Renee C Langhals
(74) *Attorney, Agent, or Firm* — Troutman Pepper Hamilton Sanders LLP; Ryan Schneider; Lauren Giambalvo

(57) ABSTRACT

A system for instrument guidance is disclosed. The system can include an instrument guide device and a transducer system. The instrument guide device can include an instrument guide and an instrument guide bracket that includes a magnet, and the instrument guide bracket can be removably attachable to the instrument guide. The transducer system can include an ultrasound probe bracket that is removably attachable to an ultrasound probe. Further, the instrument guide device can removably attach to the ultrasound probe bracket. The ultrasound probe bracket can further include a first sensor and second sensor. The first sensor can wirelessly track a position of the magnet to determine position data of the instrument guidance system. And the second sensor can provide power or disengage power to the instrument guidance device when the instrument guide is attached or detached, respectively.

15 Claims, 5 Drawing Sheets

Related U.S. Application Data

(60) Provisional application No. 62/866,950, filed on Jun. 26, 2019, provisional application No. 62/814,004, filed on Mar. 5, 2019.

(52) U.S. Cl.
CPC .............. *A61B 8/461* (2013.01); *A61B 8/463* (2013.01); *A61B 8/5207* (2013.01); *A61B 34/20* (2016.02); *A61B 8/4227* (2013.01); *A61B 2034/2063* (2016.02); *A61B 2560/0214* (2013.01)

(56) References Cited

U.S. PATENT DOCUMENTS

| | | | |
|---|---|---|---|
| 4,497,325 | A | 2/1985 | Wedel |
| 4,567,896 | A | 2/1986 | Barnea et al. |
| 4,576,175 | A | 3/1986 | Epstein |
| 4,681,103 | A | 7/1987 | Boner et al. |
| 4,898,178 | A | 2/1990 | Wedel |
| 4,899,756 | A * | 2/1990 | Sonek ................. A61B 8/0833 600/461 |
| 5,052,396 | A | 10/1991 | Wedel et al. |
| 5,100,387 | A | 3/1992 | Ng |
| 5,211,165 | A | 5/1993 | Dumoulin et al. |
| 5,224,680 | A | 7/1993 | Greenstein et al. |
| 5,235,987 | A | 8/1993 | Wolfe |
| 5,647,373 | A | 7/1997 | Paltieli |
| 5,676,673 | A | 10/1997 | Ferre et al. |
| 5,941,889 | A | 8/1999 | Cermak |
| 6,203,499 | B1 | 3/2001 | Imling et al. |
| 6,216,029 | B1 * | 4/2001 | Paltieli ................. A61B 8/0833 600/427 |
| 6,296,614 | B1 | 10/2001 | Pruter |
| 6,361,499 | B1 | 3/2002 | Bates et al. |
| 6,368,280 | B1 | 4/2002 | Cermak et al. |
| 6,379,307 | B1 | 4/2002 | Filly et al. |
| 6,475,152 | B1 | 11/2002 | Kelly, Jr. et al. |
| 6,695,786 | B2 | 2/2004 | Wang et al. |
| 6,743,177 | B2 | 6/2004 | Ito |
| 6,908,433 | B1 | 6/2005 | Pruter |
| 8,073,529 | B2 | 12/2011 | Cermak et al. |
| 8,147,408 | B2 | 4/2012 | Bunce et al. |
| 8,257,264 | B2 | 9/2012 | Park et al. |
| 8,449,531 | B2 | 5/2013 | Whitmore, III et al. |
| 8,527,033 | B1 | 9/2013 | Williams et al. |
| 8,556,815 | B2 | 10/2013 | Pelissier et al. |
| 8,688,196 | B2 | 4/2014 | Whitmore, III et al. |
| 8,852,111 | B2 | 10/2014 | Park et al. |
| 9,459,087 | B2 | 10/2016 | Dunbar et al. |
| 9,492,097 | B2 | 11/2016 | Wilkes et al. |
| 9,554,716 | B2 | 1/2017 | Burnside et al. |
| 9,597,008 | B2 | 3/2017 | Henkel et al. |
| 9,913,642 | B2 | 3/2018 | Leimbach et al. |
| 10,434,278 | B2 | 10/2019 | Dunbar et al. |
| 10,449,330 | B2 | 10/2019 | Newman et al. |
| 2003/0171681 | A1 * | 9/2003 | Weilandt ............ A61B 17/3403 600/464 |
| 2005/0033315 | A1 | 2/2005 | Hankins |
| 2005/0059891 | A1 * | 3/2005 | Kosaku ............... A61B 17/3403 600/439 |
| 2005/0267373 | A1 * | 12/2005 | Lee ....................... A61B 8/0841 600/471 |
| 2006/0129046 | A1 * | 6/2006 | Stevens ................ A61B 8/0833 600/464 |
| 2007/0049822 | A1 * | 3/2007 | Bunce .................. A61B 17/3403 600/437 |
| 2007/0276253 | A1 | 11/2007 | Park et al. |
| 2010/0160787 | A1 | 6/2010 | Gorzitze |
| 2010/0312121 | A1 | 12/2010 | Guan |
| 2011/0282188 | A1 * | 11/2011 | Burnside ................ A61B 34/25 600/424 |
| 2012/0071749 | A1 * | 3/2012 | Xu ........................ A61B 6/5247 600/411 |
| 2012/0143055 | A1 * | 6/2012 | Ng .......................... A61B 8/483 600/439 |
| 2012/0165679 | A1 | 6/2012 | Orome et al. |
| 2014/0228685 | A1 * | 8/2014 | Eelbode .............. A61M 5/3287 600/439 |
| 2014/0257080 | A1 | 9/2014 | Dunbar et al. |
| 2017/0196535 | A1 * | 7/2017 | Arai .................... A61B 18/1477 |
| 2018/0366035 | A1 * | 12/2018 | Dunbar ................ A61B 8/4254 |
| 2019/0223958 | A1 * | 7/2019 | Kohli .................... A61B 34/20 |

OTHER PUBLICATIONS

What is RFID? Bar Code Graphics Inc. https://www.epc-rfid.info/rfid, Web Archive date of Sep. 2, 2018. (Year: 2018).*

* cited by examiner

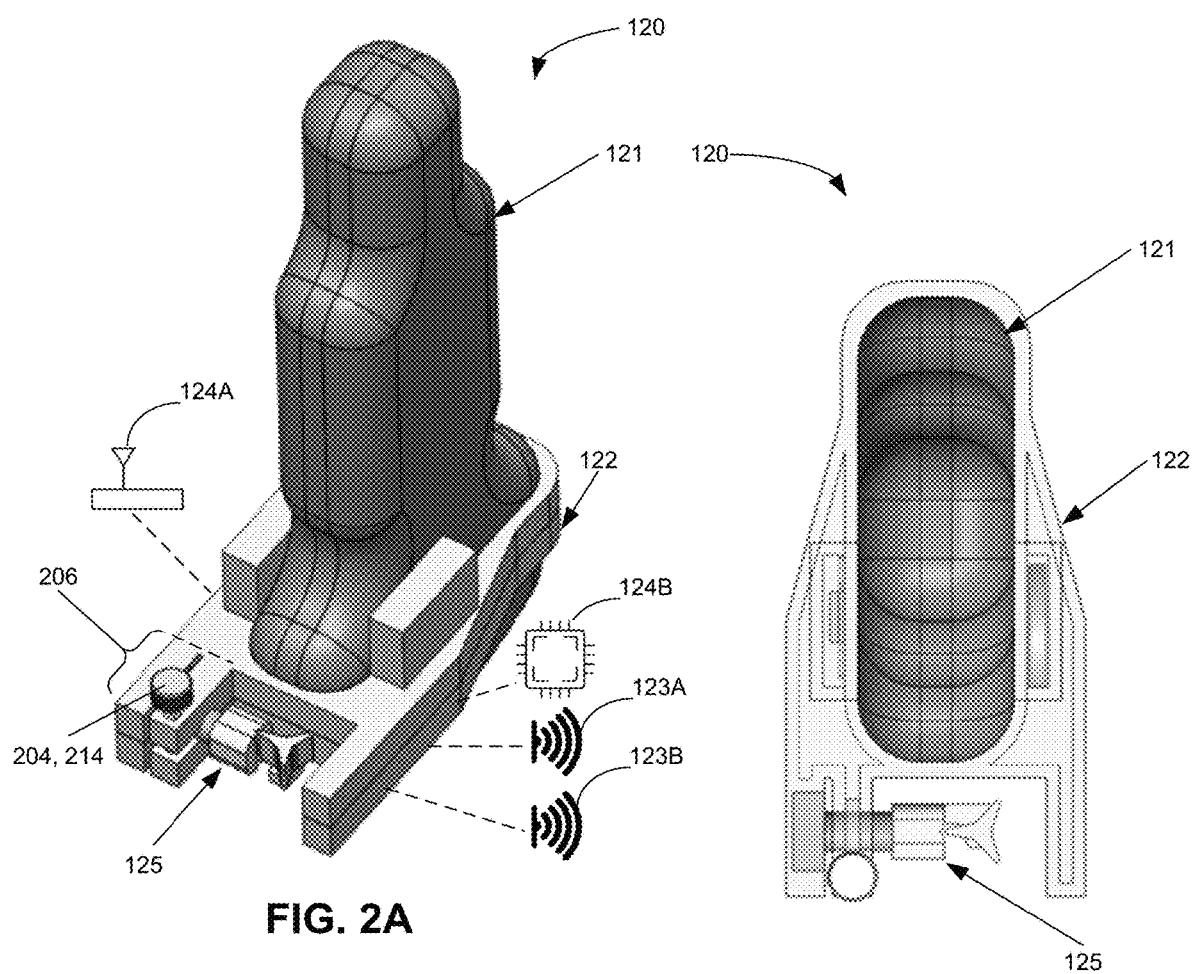
FIG. 2A
FIG. 2B
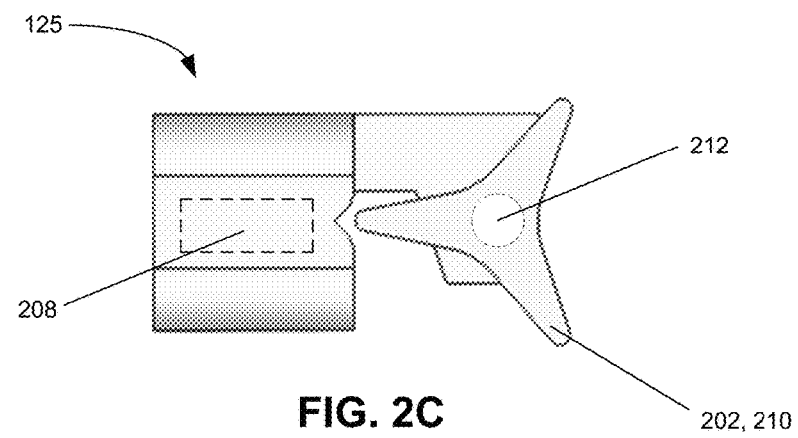
FIG. 2C

SYSTEMS, METHODS, AND DEVICES FOR INSTRUMENT GUIDANCE

CROSS-REFERENCE TO RELATED APPLICATION

This Application is a Continuation of U.S. patent application Ser. No. 16/810,569, filed Mar. 5, 2020, which claims the benefit of, and priority under 35 U.S.C. § 119(e) to, U.S. Provisional Patent Application Nos. 62/814,004 and 62/866,950, filed Mar. 5, 2019 and Jun. 26, 2019, respectively, the contents of which are hereby incorporated by reference in its entirety as if fully set forth below.

FIELD OF THE INVENTION

The present invention relates generally to systems, methods, and devices for instrument guidance and, more particularly, to systems, methods, and devices for guiding the placement of instruments within the body using ultrasound imaging.

BACKGROUND

Ultrasound imaging can provide real-time two-dimensional imaging of a patient's body, which can be used to assist a healthcare professional to locate a region to insert an invasive medical device (e.g., a needle or a cylindrical instrument such a trocar, etc.). Once the healthcare professional locates the correct insertion point, the healthcare professional may then begin the medical procedure, such as insertion of a catheter, administration of a local anesthetic, or removal of tissue as in a biopsy. Determining at what orientation to insert the invasive medical device to ensure an unobstructed path to the target is challenging, as the ultrasound monitor can only display structures within the patient's body. It can also be difficult to tell what path the medical device will follow before the device enters the patient's body. Furthermore, after the medical device enters the patient's body, it can be difficult to accurately track the path and position of the medical device on the ultrasound monitor. Using the needle as an example—unless the needle is positioned exactly in-plane with the image, the needle may not be visible or may only be partially visible, which means that the needle location or, more importantly, the location of the needle tip is not precisely known. As such, the healthcare professional may make numerous attempts to insert the device before properly entering a tissue mass or penetrating a blood vessel. Further, in the case of a nerve, the healthcare professional can often only estimate the location of the needle end if it is not visible on the ultrasound image. As a result, patients may be injured or made to suffer unnecessary pain. From the healthcare professional's perspective, these procedures can be time consuming, and can expose the healthcare professional to liability. These and other drawbacks exist.

Accordingly, there is a need for improved systems, methods, and devices that provide guided instrument placement within the body.

SUMMARY

Aspects of the disclosed technology include systems, methods and devices for guided instrument placement. Consistent with the disclosed embodiments, an exemplary device can include an instrument guide device and a transducer system. The instrument guide device can comprise an instrument guide, an instrument guide insert, and an instrument guide bracket. The instrument guide can include a first aperture, a magnet, and one or more protrusions. The instrument guide can be configured to secure at least one instrument. Further, the instrument guide can be adaptable to secure instruments of different sizes. Turning to the instrument guide bracket, the instrument guide bracket can be removably attachable to the instrument guide when at least a first protrusion of the instrument guide engages with at least a first opening of the instrument guide bracket.

The transducer system can comprise an ultrasound probe bracket and an ultrasound probe. The ultrasound probe bracket can include a first sensor, a transceiver, and a processor. The first sensor can be configured to determine a position of the instrument guide device by wirelessly tracking the magnet located in the instrument guide. That is, as the instrument guide is moved around a body, the first sensor tracks the magnet to determine the position of the instrument guide device. The ultrasound probe bracket further includes a transceiver that is configured to receive the position of the instrument guide device from the first sensor, and then output the position to an external device (e.g., a computing device). The ultrasound probe bracket can further include a cutout sized to allow the instrument guide device to fit within and a member (e.g., snap features, protrusions, cutouts, and/or spring-loaded inserts) that allows the instrument guide device to removably attach to the ultrasound probe bracket. In some examples, rather than the cutout, the ultrasound probe bracket can include a single or pair of protruding features that provide attachment to the instrument guide bracket. The ultrasound probe bracket can be sized to fit around the ultrasound probe and can be removably attachable to the ultrasound probe. The ultrasound probe can generate and send image information to the processor. Then, the processor can generate position data using the position of the instrument guide device and/or the image information.

In some embodiments, the instrument guide can include a plurality of instrument guide inserts having different instrument sizes and/or gauges.

In some embodiments, the instrument guide can include a single insert that can be rotated to different positions to create different apertures sized to accommodate different instrument sizes and/or gauges.

According to some embodiments, the instrument guide insert can be sized to fit within the first aperture, wherein the at least one instrument is secured to the instrument guide insert.

In some embodiments, a first insert can be positioned into a second opening of the instrument guide bracket from an exterior surface of the instrument guide bracket such that when the first insert is tightened it deforms the instrument guide bracket and reduces the size of a cutout in the instrument guide bracket within which at least one protrusion of the one or more protrusions rotates. Also, the first insert can be further positioned into the instrument guide along a central axis such that the instrument guide is rotatable along the central axis and that the first insert induces friction that causes the instrument guide to maintain its orientation.

According to some embodiments, the ultrasound probe bracket is adaptable to fit a plurality of geometries.

In some embodiments, in response to movement of the instrument guidance system, the instrument guide remains positioned in the same orientation as a first instrument secured by the instrument guide.

In some embodiments, a first instrument is removably attachable to the instrument guide when the first instrument is inserted within a second aperture perpendicular to the instrument guide's axis of rotation.

In some embodiments, the instrument guide includes a rotation lock configured to allow and prevent rotation of the instrument guide.

According to some embodiments, the processor of the ultrasound probe bracket can determine whether the instrument guide is attached to the instrument guidance system. Also, the ultrasound probe bracket can include a second sensor configured to provide power and disengage power to the instrument guidance device when the instrument guide is attached or detached, respectively. It should be noted that the first sensor can perform all or some of the functions of the second sensor and vice versa.

An exemplary method includes a computing device receiving imaging data from an ultrasound device, which the computing device can display. The computing device can also communicate with an instrument guide device to receive position data that indicates an angle of an instrument attached to the instrument guide device. The computing device is preprogrammed with: 1) the physical location of the instrument guide device's axis of rotation relative to the imaging surface of the ultrasound transducer; and 2) an algorithm to compute the pixel distance on the display corresponding to a physical metric in the ultrasound image (e.g., centimeters) at any given imaging depth. Then, the computing device can determine where the trajectory of the instrument should lie on the ultrasound image in real-time. The generated image can then be displayed on a screen of the computing device, for example, as a graphical user interface (GUI).

In some embodiments, the ultrasound device can receive the position data from the instrument guide device and can generate the image overlay in a manner similar or identical to that disclosed above in reference to the computing device.

In some embodiments, the first sensor can be included in the instrument guide device rather than in the ultrasound probe bracket. In these embodiments, the ultrasound probe cover can include sealed, electrical ports, or contacts to enable electrical connection between the first sensor in the instrument guide device and the processor and/or transceiver in the ultrasound probe bracket, while maintaining a sterile barrier.

In some embodiments, the instrument guide device can be permanently coupled to the ultrasound probe cover, through methods such as adhesive or thermal bonding, such that attachment of the ultrasound probe cover and instrument guide device over/onto the ultrasound probe bracket can occur simultaneously.

Further features of the disclosed design, and the advantages offered thereby, are explained in greater detail hereinafter with reference to specific embodiments illustrated in the accompanying drawings, wherein like elements are indicated by like reference designators.

BRIEF DESCRIPTION OF THE DRAWINGS

Reference will now be made to the accompanying drawings, which are not necessarily drawn to scale, are incorporated into and constitute a portion of this disclosure, illustrate various implementations and aspects of the disclosed technology, and, together with the description, serve to explain the principles of the disclosed technology. In the drawings:

FIG. 2A is an isometric view of an instrument guidance device, in accordance with some examples of the present disclosure;

FIG. 2B is a top view of an instrument guidance device, in accordance with some examples of the present disclosure;

FIG. 2C is a top view of an instrument guide device, in accordance with some examples of the present disclosure;

DETAILED DESCRIPTION

Some implementations of the disclosed technology will be described more fully with reference to the accompanying drawings. This disclosed technology can be embodied in many different forms, however, and should not be construed as limited to the implementations set forth herein. The components described hereinafter as making up various elements of the disclosed technology are intended to be illustrative and not restrictive. Many suitable components that would perform the same or similar functions as components described herein are intended to be embraced within the scope of the disclosed electronic devices and methods. Such other components not described herein can include, but are not limited to, for example, components developed after development of the disclosed technology.

It is also to be understood that the mention of one or more method steps does not imply that the methods steps must be performed in a particular order or preclude the presence of additional method steps or intervening method steps between the steps expressly identified.

Reference will now be made in detail to exemplary embodiments of the disclosed technology, examples of which are illustrated in the accompanying drawings and disclosed herein. Wherever convenient, the same reference numbers will be used throughout the drawings to refer to the same or like parts.

Figure 1:
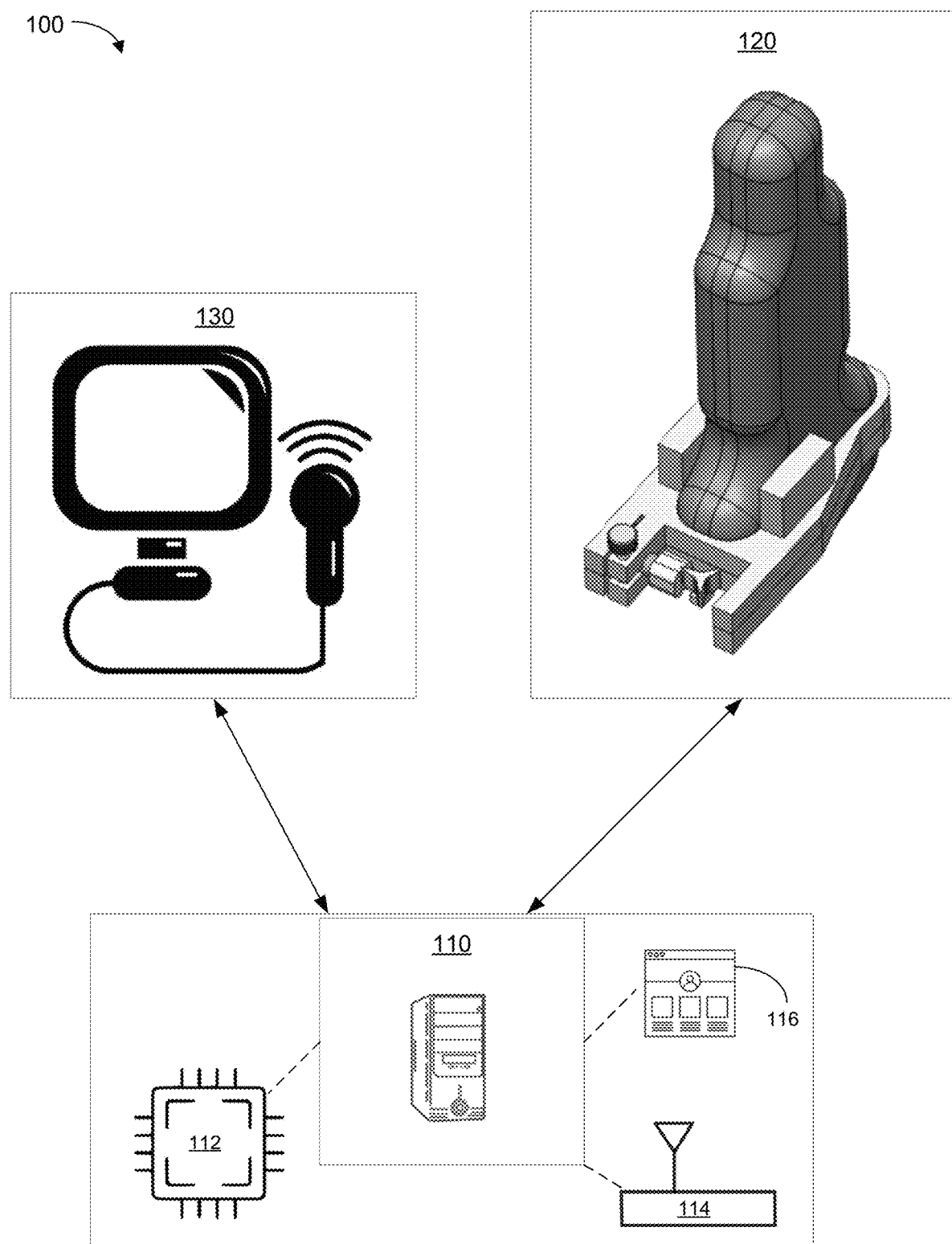
FIG. 1 is an example system for instrument guidance, in accordance with some examples of the present disclosure.

FIG. 1 is a schematic of an exemplary system 100 used for instrument guidance. As shown, the system 100 includes a computing device 110, an instrument guidance device 120, and an ultrasound device 130. The instrument guide device 125 can include a first aperture, a magnet, and one or more protrusions. In some examples, rather than the magnet the instrument guide device 125 can include a sensing element (e.g., a potentiometer, a feature to engage with a potentiometer, an optical sensing element that can be used by an optical sensor, and/or a capacitive sensing element that can be used by a capacitive sensor). Further, the sensing element can be contained in an instrument guide insert that is attached to the instrument guide device 125. The computing device 110 can include one or more processors 112, transceiver 114, and display 116, among other things. The computing device 110 can communicate with the instrument guidance device 120 and/or the ultrasound device 130.

As one skilled in the art would understand, the ultrasound device 130 can emit high-frequency sound waves that, when a transducer of the ultrasound device 130 is placed against a body, reflect off body structures. The ultrasound device 130 can then receive the waves and can use the waves to create imaging data. Here, the ultrasound device 130 can send the imaging data in real-time to the computing device 110.

As shown in FIGS. 2A-C, the instrument guidance device 120 can include ultrasound probe 121, ultrasound probe bracket 122, instrument guide device 125, first sensor 123A, second sensor 123B, ultrasound transceiver 124A, and ultrasound processor 124B. The ultrasound transceiver 124A can be located in ultrasound probe bracket 122 and can transmit various data including position data and a unique identifier for the ultrasound probe 121. The first sensor 123A and/or second sensor 123B can be a magnetoresistive sensor, Hall effect sensor, magnetic potentiometer, and/or the like that can be configured to detect a magnetic field and changes as the magnetic field is rotated and/or translated. The instrument guide device can further comprise an instrument guide insert 202, a first insert 204, an instrument guide bracket 206, and a magnet 208. The instrument guide insert 202 can be a rotatable instrument guide insert 210 insertable into a first aperture 212 in the instrument guide. The first insert 204 can be a rotation lock 214 configured to allow and prevent rotation of the instrument guide. The magnet 208 is within the instrument guide.

Turning to use of the instrument guidance device 120, a user (e.g., a physician) can place the instrument guidance device 120 near a portion of the body (e.g., the neck) to approximate an area to insert an instrument. The instrument guide device 125 of the instrument guidance device 120 can hold one or more instruments of differing sizes, which can be attributed to a multi-faceted block which can rotate beside an open channel to create a closed channel of variable size (shown in FIG. 2C). Additionally or alternatively, the instrument guide device 125 can include a plurality of disposable instrument inserts that are each designed to fit a specific instrument guide, but each has a consistent outer geometry to attach. Also, the instrument guide device 125 can include a single instrument insert that includes a plurality of faces or a single continuous face that when the instrument insert is twisted, changes the size of a second aperture created between the instrument insert and the instrument guide device 125, which can allow for different instrument sizes and/or gauges to be used. In some examples, the instrument guide device 125 can be a single disposable instrument guide that accepts a plurality of instrument sizes. An instrument inserted into the instrument guide device 125 can be indirectly and/or removably attached or attachable to the ultrasound probe 121.

As the user moves the instrument guidance device 120, the magnet can change orientation accordingly; however, the magnet can be in a fixed position in rotating element of the instrument guidance device 120, such that the magnet does not change the angle and/or position relative to the rotating element. The first sensor 123A can wirelessly track the magnet, using for example magnetoresistive properties that rely on the magnetic field, to determine an orientation (e.g., angle) and/or position of the instrument guide device 125. Then, the ultrasound processor 124B can generate position data (e.g., angle and positioning values), which can be in relation to the surface of the ultrasound probe 121. More specifically, the first sensor 123A can send a voltage within a range (e.g., 0-3.3 volts) corresponding to the angle of the magnet to the ultrasound processor 124B. The ultrasound processor 124B can convert this voltage to an integer within a range (e.g., 0-1023 for a 10-bit analog-to-digital conversion). Using the transceiver 124A, the instrument guidance device 120 can send the position data, using for example Bluetooth® technology, to the computing device 110.

Furthermore, the second sensor 123B can provide power to the instrument guidance device 120 when the instrument guide device 125 is attached. Conversely, the second sensor 123B can disengage power to the instrument guidance device 120 when the instrument guide device 125 is detached.

Referring to the computing device 110, the computing device 110 can receive the imaging data and the position data from the ultrasound device 130 and the instrument guidance device 120, respectively. The computing device 110 can then generate an image overlay using the imaging data and the position data. The image overlay can project the position data onto the imaging data. Further, the computing device 110 can display the image overlay on the display 116 of the computing device 110 or in some examples, the computing device 110 can send the image overlay to an external device and/or the ultrasound device 130 that displays the image overlay. Additionally or alternatively, the computing device 110 can project the image overlay over a screen of the ultrasound device 130, using for example lasers, or by placing a see-through screen over the screen of the ultrasound sound device 130. In other words, the position of an instrument can be mapped onto the imaging data that shows an image of the body. Thus, in real-time, for example, a healthcare professional can see the position of an instrument and a blood vessel, which can eliminate errors.

In some examples, the instrument guidance device 120 may need to be assembled prior to use. The following embodiment refers to an instrument guide insert that is used with the instrument guide device 125 in place of the multi-faceted block (discussed above). The instrument guide insert can be positioned over the instrument guide device 125 and pressed into the first aperture, which may make a snapping noise when inserted. Next, the instrument guide device 125 can be attached to an instrument guide bracket that contains holes that the one or more protrusions are sized to fit in. Then, ultrasound probe bracket 122 can be attached to the ultrasound probe 121, for example, by aligning the ultrasound probe bracket 122 with the ultrasound probe 121 and pushing upwards until a clicking/snapping noise is audible and/or a tactile cue is felt. Additionally or alternatively, the ultrasound probe 121 can be used to assemble the ultrasound probe bracket 122 in a pivoting motion. After attachment, an ultrasound probe cover can be placed over the ultrasound probe bracket 122 and the ultrasound probe 121. Then, the assembled instrument guide device 125 can be attached to the ultrasound probe bracket 122 over the ultrasound probe cover to form a sterile barrier. In some examples, the instrument guide device 125 can attach to the ultrasound probe bracket 122 via a magnetic attachment, an adhesive attachment, a hook-and-loop strips attachment, and/or the like.

Referring to the instrument guide insert, the instrument guide insert can include the one or more protrusions and/or one or more features that align with the one or more protrusions and/or the one or more features on the instrument guide device 125 such that the instrument guide insert snaps into pre-defined rotational positions as it is rotated to select apertures (e.g., a set of apertures) for different instrument sizes. Also, the instrument guide insert can be rotated one way to close the second aperture between the instrument guide insert and the instrument guide device 125, and rotated another way to open the second aperture between the instrument guide insert and the instrument guide device 125, such that the first instrument (e.g., the needle) can be removed from the instrument guidance device 120 in a direction perpendicular to the first instrument's central axis. The instrument guide insert and/or the instrument guide device 125 can include a button and/or a lever that can be actuated to open and close the second aperture created between the instrument guide insert and instrument guide device 125.

Figure 3A:
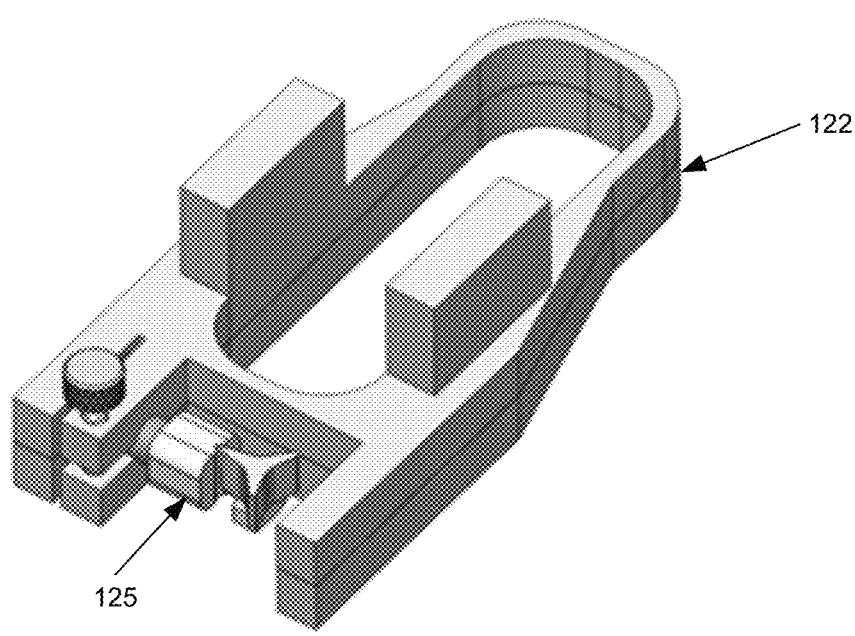
FIG. 3A is an isometric view of an ultrasound probe bracket and an attached instrument guide device, in accordance with some examples of the present disclosure.
Figure 3B:
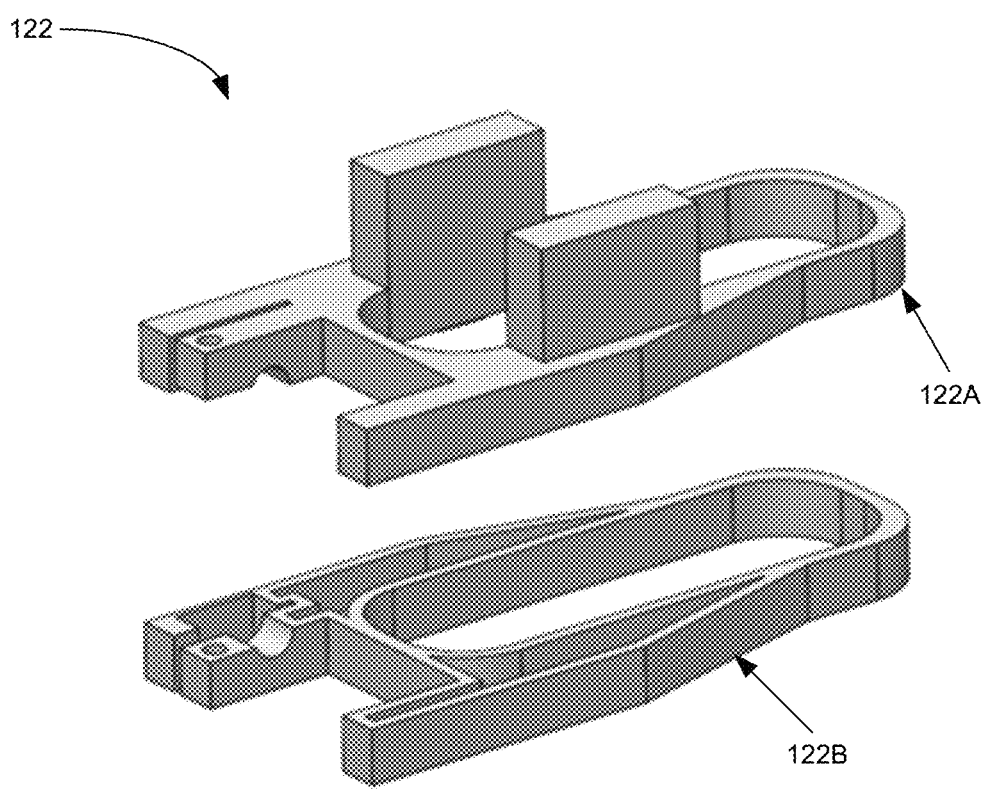
FIG. 3B is an exploded view of an ultrasound probe bracket, in accordance with some examples of the present disclosure.

The ultrasound probe bracket 122 can include top portion 122A and bottom portion 122B (shown in FIG. 3B) that can be joined together (e.g., snapped into place) to form the ultrasound probe bracket 122. In some examples, the ultrasound probe bracket 122 can be opened about a hinge, fit around the ultrasound probe 121, and then closed together while maintaining alignment. In other examples, the ultrasound probe bracket 122 can include a pin snap fit or a latch to join members of the ultrasound probe bracket 122. Thus, the ultrasound probe bracket 122 may fit the geometry of various sized ultrasound probes. Further, the ultrasound probe bracket 122 can be split into a plurality of pieces (e.g., halves) and/or can be opened and/or closed around the ultrasound probe 121.

Figure 4:
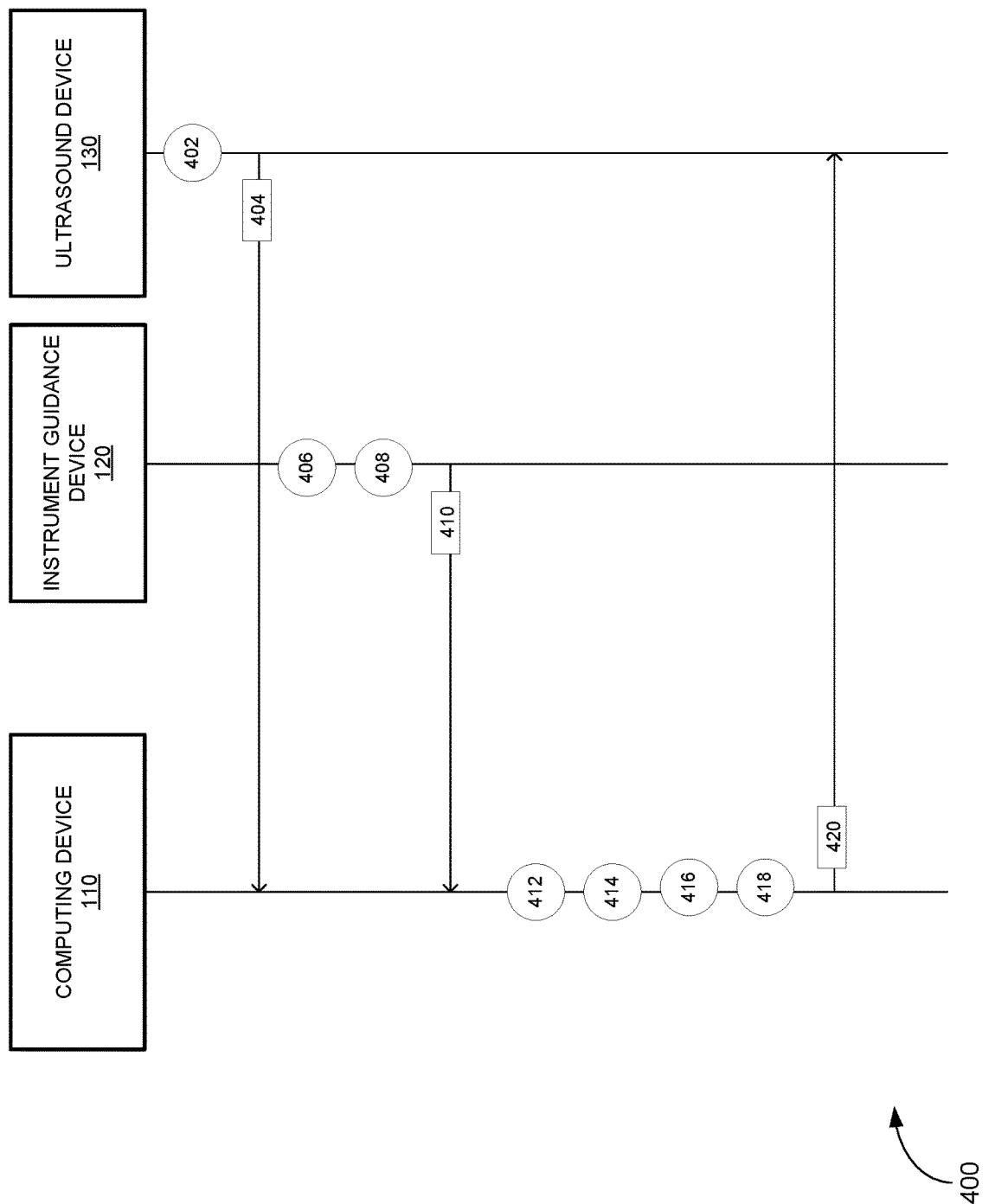
FIG. 4 is an example timing diagram for instrument guidance, in accordance with some examples of the present disclosure.

FIG. 4 shows a timing diagram of a method 400 for instrument guidance (e.g., using system 100). Thus, the method 400 can be performed by the computing device 110, the instrument guidance device 120, and the ultrasound device 130. Further, each of the aforementioned devices may be in communication with one another to perform the method 400.

At 402, the ultrasound device 130 generates imaging data, i.e., an ultrasound image of a portion of a person's body. Then, at 404, the ultrasound device 130 sends the imaging data to the computing device 110. Next, at 406, the instrument guidance device 120, using the first sensor 123A, can determine an angle of the instrument guide device 125 by tracking a magnet that is included within the instrument guide device 125. The instrument guidance device 120 then generates, at 408, position data based on the angle of the instrument guide device 125. At 410, the instrument guidance device 120 sends the position data to the computing device 110. The computing device can, at 412, compute the pixel distance, for example on the display 116 or the ultrasound device 130, corresponding to a physical metric in the ultrasound image (e.g., centimeters) at the present imaging depth.

Next, at 414, the computing device 110 can compute how the position data should be displayed at the present imaging depth given the pixel distance determined at 412. At 416, the computing device 110 can generate an image overlay that projects the position data onto the imaging data, which can be displayed by the computing device 110, at 418. At 420, the computing device 110 can send the image overlay to the ultrasound device 130 (as shown) and/or an external device.

Figure 5:
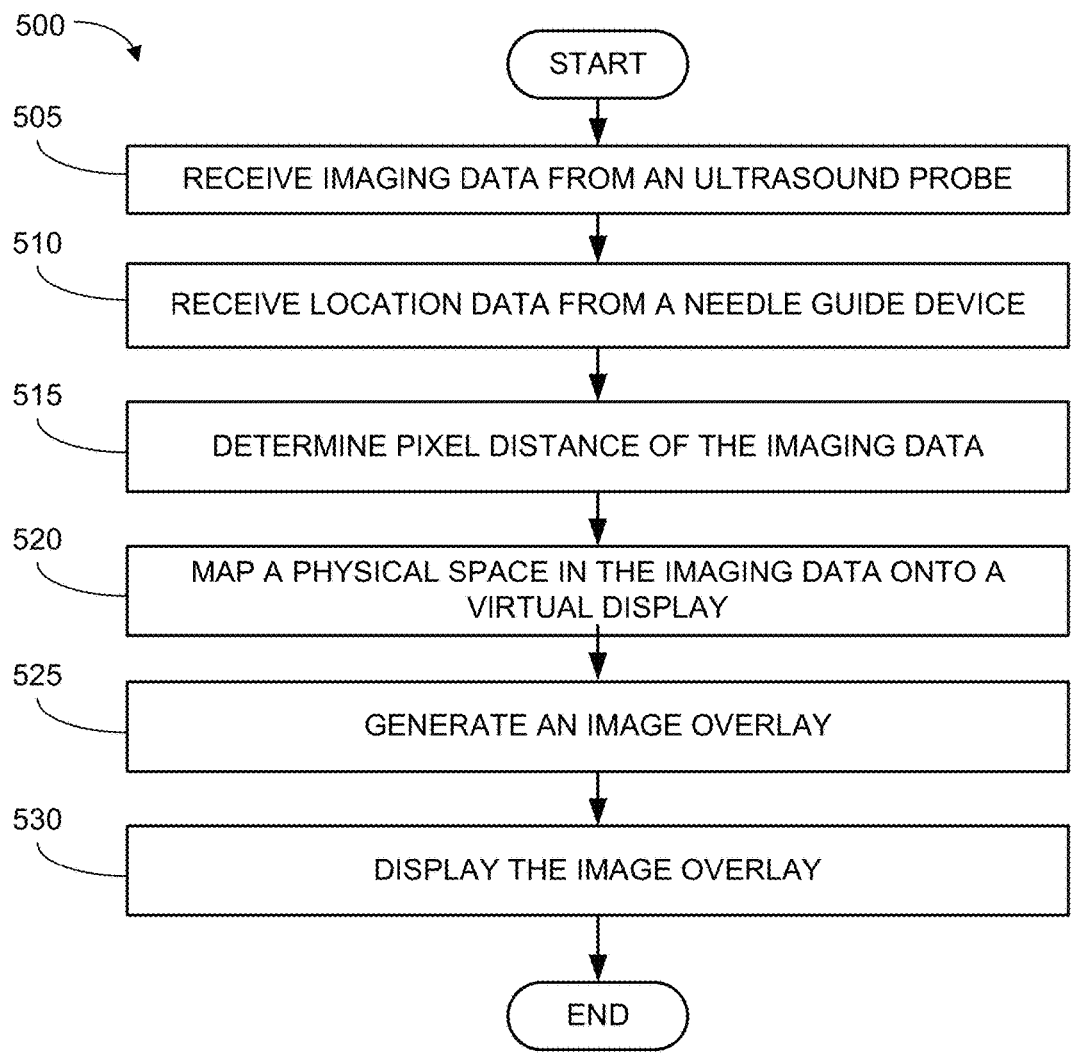
FIG. 5 is an example flow chart of a method for instrument guidance, in accordance with some examples of the present disclosure.

FIG. 5 illustrates a flow chart of a method 500 for instrument guidance. The method 500 is written from the perspective of the computing device 110 that can communicate with the instrument guidance device 120, the ultrasound device 130, and/or an external device. Using the method 500 can allow the computing device 110 to provide real-time imaging of both a patient's body and an instrument in relation to the patient's body.

At 505, the computing device 110 can receive imaging data from the ultrasound device 130. The computing device 110 can also receive position data from the instrument guidance device 120, at 510. At 515, the computing device 110 can determine pixel distance on the display corresponding to a physical metric (e.g., centimeters) in the ultrasound image at the present imaging depth. At 520, the computing device 110 can map a physical space in the imaging data onto a virtual display based on the pixel distance. Then, at 525, the computing device 110 can generate an image overlay that maps the position data (e.g., position of the needle and an trajectory of the needle) over the imaging data, such that the position of the instrument is shown in relation to the portion of the body being viewed by the ultrasound device 130. At 530, the computing device 110 can display the image overlay.

Throughout the specification and the claims, the following terms take at least the meanings explicitly associated herein, unless the context clearly dictates otherwise. The term "or" is intended to mean an inclusive "or." Further, the terms "a," "an," and "the" are intended to mean one or more unless specified otherwise or clear from the context to be directed to a singular form.

In this description, numerous specific details have been set forth. It is to be understood, however, that implementations of the disclosed technology can be practiced without these specific details. In other instances, well-known methods, structures and techniques have not been shown in detail in order not to obscure an understanding of this description. References to "one embodiment," "an embodiment," "some embodiments," "example embodiment," "various embodiments," "one implementation," "an implementation," "example implementation," "various implementations," "some implementations," etc., indicate that the implementation(s) of the disclosed technology so described can include a particular feature, structure, or characteristic, but not every implementation necessarily includes the particular feature, structure, or characteristic. Further, repeated use of the phrase "in one implementation" does not necessarily refer to the same implementation, although it can.

As used herein, unless otherwise specified the use of the ordinal adjectives "first," "second," "third," etc., to describe a common object, merely indicate that different instances of like objects are being referred to, and are not intended to imply that the objects so described must be in a given sequence, either temporally, spatially, in ranking, or in any other manner.

While certain implementations of the disclosed technology have been described in connection with what is presently considered to be the most practical and various implementations, it is to be understood that the disclosed technology is not to be limited to the disclosed implementations, but on the contrary, is intended to cover various modifications and equivalent arrangements included within the scope of the appended claims. Although specific terms are employed herein, they are used in a generic and descriptive sense only and not for purposes of limitation.

This written description uses examples to disclose certain implementations of the disclosed technology, including the best mode, and also to enable any person skilled in the art to practice certain implementations of the disclosed technology, including making and using any devices or systems and performing any incorporated methods. The patentable scope of certain implementations of the disclosed technology is defined in the claims, and can include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. An instrument guidance device comprising:
   an instrument guide device comprising:

an instrument guide comprising one or more protrusions;

an instrument guide bracket comprising openings located at one or more side surfaces; and a magnet;

a first insert;

a tracking system comprising tracking components; and an ultrasound probe bracket comprising the tracking components of the tracking system;

wherein the instrument guide device is free of tracking components of the tracking system;

wherein the instrument guide is configured to:
be rotatably attached to the instrument guide bracket when at least a first protrusion of the one or more protrusions of the instrument guide engages with at least a first opening of the openings of the instrument guide bracket;

house the magnet in a fixed and known position and orientation relative to the instrument guide; and releasably secure an instrument inserted through the instrument guide such that an insertable portion of the instrument is removably inserted into an object;

wherein the first insert is insertable into a second opening of the openings of the instrument guide bracket from an exterior surface of the instrument guide bracket such that the first insert intersects with a portion of the instrument guide to lock and/or induce friction on rotation of the instrument guide;

wherein the tracking system is configured to wirelessly track the magnet of the instrument guide device to determine and monitor changes in the orientation and/or position of the instrument guide; and wherein the ultrasound probe bracket is configured to releasably secure:
a probe of an imaging system; and
the instrument guide device.

2. The instrument guidance device of claim 1, wherein the instrument guide device further comprises a rotation lock configured to allow and prevent rotation of the instrument guide.

3. The instrument guidance device of claim 1, wherein tracking components of the tracking system comprise:
a first sensor;
a first processor; and
a first transceiver;
wherein the first sensor is distal the instrument guide device and configured to:
collect data representative of the magnet; and
produce data representative of the orientation and/or position of the instrument guide;
wherein the first processor is configured to:
receive the data from the first sensor; and
process the received data; and
wherein the first transceiver is configured to:
receive the processed data from the first processor; and
wirelessly transmit the processed data.

4. The instrument guidance device of claim 3, wherein the tracking system further comprises a second sensor configured to:
provide power to the tracking components of the tracking system when the instrument guide device is attached to the ultrasound probe bracket; and
disengage power to the tracking components of the tracking system when the instrument guide is detached from the ultrasound probe bracket.

5. The instrument guidance device of claim 3, wherein the first sensor collects data representative of a magnetic field of the magnet; and
wherein the orientation and/or position of the instrument guide device is determined by one or more of magnitude and orientation of the magnetic field.

6. The instrument guidance device of claim 3, wherein the instrument guide bracket of the instrument guide device is configured to removably attach to the ultrasound probe bracket in a fixed and known orientation and position;
wherein the ultrasound probe bracket is further configured to releasably secure the probe of the imaging system in a fixed and known orientation and position; and
wherein the first processor of the tracking system is further configured to determine the orientation and/or position of the instrument guide of the instrument guide device relative to the probe of the imaging system.

7. The instrument guidance device of claim 1, wherein:
the instrument guide further comprises a first aperture;
the instrument guide device further comprises an instrument guide insert that is sized to fit within the first aperture of the instrument guide; and
an instrument channel through the instrument guide is sized to accommodate the instrument size of the instrument when releasably secured by the instrument guide.

8. The instrument guidance device of claim 7, wherein the instrument guide insert is selected from the group consisting of two or more different instrument guide inserts, each different instrument guide insert being configured to accommodate a different instrument size of the instrument.

9. The instrument guidance device of claim 7, wherein surfaces of the instrument guide insert and the instrument guide cooperate to form two or more different configurations via rotation of the instrument guide insert relative to the instrument guide, wherein two of the different configurations comprise:
an engagement configuration; and
a disengagement configuration;
wherein in the engagement configuration, the instrument channel is configured for insertion and retention of the insertable portion of the instrument; and
wherein in the disengagement configuration, the surfaces of the instrument guide insert and the instrument guide form a cavity to an outer surface of the instrument guide, configured to facilitate movement of the instrument in a direction perpendicular to the instrument channel.

10. The instrument guidance device of claim 1, wherein the instrument guide device further comprises a rotatable instrument guide insert having faces;
wherein when the instrument guide insert is rotated, an instrument channel is defined through the instrument guide, the instrument channel sized to accommodate the instrument size of the instrument when releasably secured by the instrument guide; and
wherein at least a portion of the faces of the instrument guide insert each correspond to different instrument sizes, such that rotation of the instrument guide insert provides a selection of different instrument channel sizes depending on the instrument size of the instrument.

11. An instrument guidance system comprising:
a computing device;
the instrument guidance device of claim 1; and
an imaging system configured to:
generate imaging data representative of a portion of a human body; and send the imaging data to the computing device;
wherein the computing device is configured to:
receive, by a second transceiver of the computing device, the imaging data from the imaging system;
receive, by the second transceiver, the processed data wirelessly transmitted by the first transceiver;
determine, by a second processor of the computing device, how physical space in the imaging data is mapped on a virtual display;
generate, by the second processor, an image overlay that projects the processed data onto the imaging data, wherein an instrument trajectory is shown in relation to the imaging data; and
display, by a screen of the computing device, the image overlay.

12. An instrument guidance device comprising:
an instrument guide device comprising:
an instrument guide comprising one or more protrusions;
an instrument guide bracket comprising openings located at one or more side surfaces; and
a magnet;
a first insert;
a tracking system comprising tracking components; and
an ultrasound probe bracket comprising the tracking components of the tracking system;
wherein the instrument guide device is free of tracking components of the tracking system;
wherein the instrument guide is configured to:
be rotatably attached to the instrument guide bracket when at least a first protrusion of the one or more protrusions of the instrument guide engages with at least a first opening of the openings of the instrument guide bracket;
house the magnet in a fixed and known position and orientation relative to the instrument guide; and
releasably secure an instrument inserted through the instrument guide such that an insertable portion of the instrument is removably inserted into an object;
wherein the first insert is insertable into a second opening of the openings of the instrument guide bracket from an exterior surface of the instrument guide bracket such that when the first insert is tightened, the first insert deforms the instrument guide bracket and reduces the size of a cutout in the instrument guide bracket within which at least one protrusion of the one or more protrusions of the instrument guide rotates;
wherein the tracking system is configured to wirelessly track the magnet of the instrument guide device to determine and monitor changes in the orientation and/or position of the instrument guide; and
wherein the ultrasound probe bracket is configured to releasably secure:
a probe of an imaging system; and
the instrument guide device.

13. An instrument guidance device comprising:
a first insert;
an instrument guide device comprising:
an instrument guide comprising one or more protrusions;
an instrument guide bracket comprising openings located at one or more side surfaces; and
a magnet;
a tracking system comprising tracking components; and
an ultrasound probe bracket comprising the tracking components of the tracking system;
wherein the instrument guide device is free of tracking components of the tracking system;
wherein the instrument guide is configured to:
house the magnet in a fixed and known position and orientation relative to the instrument guide; and
releasably secure an instrument inserted through the instrument guide such that an insertable portion of the instrument is removably inserted into an object;
wherein the instrument guide bracket is rotatably attachable to the instrument guide when at least a first protrusion of the one or more protrusions of the instrument guide engages with at least a first opening of the openings of the instrument guide bracket;
wherein the first insert is insertable into a second opening of the openings of the instrument guide bracket from an exterior surface of the instrument guide bracket such that either:
the first insert intersects with a portion of the instrument guide to lock and/or induce friction on rotation of the instrument guide; or
when the first insert is tightened, the first insert deforms the instrument guide bracket and reduces the size of a cutout in the instrument guide bracket within which at least one protrusion of the one or more protrusions of the instrument guide rotates;
wherein the tracking system is configured to wirelessly track the magnet of the instrument guide device to determine and monitor changes in the orientation and/or position of the instrument guide; and
wherein the ultrasound probe bracket is configured to releasably secure:
a probe of an imaging system; and
the instrument guide device.

14. The instrument guidance device of claim 13, wherein:
the instrument guide further comprises a first aperture;
the instrument guide device further comprises an instrument guide insert that is sized to fit within the first aperture of the instrument guide; and
an instrument channel through the instrument guide is sized to accommodate the instrument size of the instrument when releasably secured by the instrument guide.

15. The instrument guidance device of claim 13, wherein the instrument guide device further comprises a rotatable instrument guide insert having faces;
wherein when the instrument guide insert is rotated, an instrument channel is defined through the instrument guide, the instrument channel sized to accommodate the instrument size of the instrument when releasably secured by the instrument guide; and
wherein at least a portion of the faces of the instrument guide insert each correspond to different instrument sizes, such that rotation of the instrument guide insert provides a selection of different instrument channel sizes depending on the instrument size of the instrument.

* * * * *